US011430552B2

(12) United States Patent
Janssen

(10) Patent No.: US 11,430,552 B2
(45) Date of Patent: Aug. 30, 2022

(54) PATIENT MONITORING LONGITUDINAL MONITORED DATA INTERPRETATION AND MANAGEMENT

(71) Applicant: GE Precision Healthcare LLC, Wauwatosa, WI (US)

(72) Inventor: Brian D. Janssen, Milwaukee, WI (US)

(73) Assignee: GE Precision Healthcare LLC, Wauwatosa, WI (US)

(*) Notice: Subject to any disclaimer, the term of this patent is extended or adjusted under 35 U.S.C. 154(b) by 61 days.

(21) Appl. No.: 16/599,403

(22) Filed: Oct. 11, 2019

(65) Prior Publication Data
US 2021/0110902 A1    Apr. 15, 2021

(51) Int. Cl.
*G16H 15/00* (2018.01)
*G16H 10/60* (2018.01)

(52) U.S. Cl.
CPC .............. *G16H 15/00* (2018.01); *G16H 10/60* (2018.01)

(58) Field of Classification Search
CPC ........ G16H 40/67; G16H 10/60; G16H 20/17; G16H 50/30; G16H 40/63; G16H 50/20; G16H 40/20; G16H 40/40; G16H 40/60; G16H 50/80; G16H 70/40; G16H 10/40; G16H 15/00; A61B 5/746; A61B 5/14532; A61B 5/0022; A61B 5/7275; A61B 5/742
See application file for complete search history.

(56) References Cited

U.S. PATENT DOCUMENTS

| 2005/0055242 | A1* | 3/2005 | Bello ..................... G16H 20/17 705/2 |
| 2009/0054735 | A1* | 2/2009 | Higgins ............... A61B 5/0006 600/300 |
| 2018/0314801 | A1 | 11/2018 | Janssen |
| 2018/0314802 | A1* | 11/2018 | Dreyer ................... G16H 40/20 |
| 2018/0315285 | A1 | 11/2018 | Janssen |
| 2019/0130332 | A1 | 5/2019 | Janssen |
| 2019/0159739 | A1* | 5/2019 | Shah .................... G08B 21/182 |

* cited by examiner

*Primary Examiner* — Maroun P Kanaan
(74) *Attorney, Agent, or Firm* — Andrus Intellectual Property Law, LLP

(57) ABSTRACT

A system and method to reduce and manage patient monitoring alarms utilizing a longitudinal, analytics-based analysis. The method includes a patient monitoring system receiving monitored data from one or more patients and generating threshold alerts for each patient based upon alert thresholds in real time. The number of alert thresholds that occur over an analysis period is compared to an enhanced alert threshold. If the number and frequency of the threshold alerts violates an enhanced alert threshold, an enhanced indicator is generated on a display for the patient being monitored. The enhanced indicator can be generated for any one or multiple monitored data types from the patient and enhances the longitudinal monitoring of the patient over an analysis period. The enhanced indicator provides a visual indicator to the monitoring technician of the occurrence of a higher than desired number of threshold alerts over the analysis period.

15 Claims, 10 Drawing Sheets

PATIENT MONITORING LONGITUDINAL MONITORED DATA INTERPRETATION AND MANAGEMENT

BACKGROUND OF THE INVENTION

The present disclosure generally relates to a system and method for managing patient monitoring alarms. More specifically, the present disclosure relates to a system and method for monitoring patient alarms that occur over a period of time using a longitudinal, analytics-based system and method to identify continuous or sustained intermittent alert/alarm conditions.

Presently, hospitals and healthcare facilities utilize patient monitoring devices to monitor various different physiological parameters of patients located in a plurality of hospital rooms. The monitored data received from each of the patients is typically relayed to a central monitoring station where a monitoring technician views all of the monitored data from a plurality of patients on one or more screens of a combined display. In some cases, monitoring technicians are tasked with continuously observing and monitoring anywhere from 36-72 or more patients simultaneously for hours on end. Although the monitoring devices generate alarms and alert conditions, often times the alert conditions occur for a brief period of time and are either self-corrected and/or are no longer present. Since the monitoring technician is tasked with monitoring a relatively large number of patients simultaneously, short and/or intermittent alerts occurring over a sustained period of time, even though visually presented to the clinician on the multi-patient monitoring display, can go unrecognized or not acted upon in a timely manner. Such alarms may appear to be an intermittent or nuisance alarm but instead are a systemic on-going issue negatively affecting the effectiveness of the monitoring session. Further, the monitoring technician is often unable to identify ongoing or sustained patterns or trends that may negatively influence patient monitoring. Such can be the case with the ECG monitoring where alerts, such as a disconnected lead or transmission failure, may occur multiple times over a monitoring period and each individual alert may not lead to any action taken by the monitoring technician or the care team. In other situations, the alerts may be indicative of an underlying problem or condition, such as poor RF connection in the area, poor lead preparation, activity of the patient that can increase artifact, and/or inappropriate alarm threshold settings as some illustrative examples.

It is generally desirable to improve the ability of the monitoring technician to recognize and contextualize alerts that take place multiple times over an analysis period and signal to the monitoring technician that the number of alerts generated over the analysis period is significant enough to require additional attention from the monitoring technician without the monitoring technician having to recognize this trend over a period of time.

SUMMARY OF THE INVENTION

The present disclosure relates to a method and system to support the reduction and better or enhanced management of patient monitoring alarms and related alarm fatigue. More specifically, the present disclosure relates to a longitudinal, analytics-based system and method to identify and alert monitoring technicians of excessive or intermittent sustained alert and alarm conditions that may negatively affect patient monitoring performance and care delivery.

In one exemplary embodiment, the present disclosure provides a method of monitoring either a plurality of patients in a care facility or an individual patient in the care facility. The method comprises receiving monitored data from each of a plurality of patients in the care facility. The monitored data can be any data related to the monitoring of the patient, including physiological data and status data of an acquisition device. The monitored data is compared to an alert threshold for the type of data. If the monitored data falls outside of an alert threshold, a threshold alert is generated.

The method of the present disclosure monitors the threshold alerts that occur over an analysis period. If the number, frequency, and/or combined duration of the threshold alerts exceeds enhanced threshold, an indicator is generated on a display that is viewed by the monitoring technician. The indicator can be shown in a patient window of a multi-patient monitoring display or, in the case of monitoring an individual patient, can be shown on the display of a single patient monitor located near the patient and at the location where the events were occurring.

In another embodiment, the present disclosure provides a multi-patient monitoring display that includes a plurality of patient windows each assigned to one of the plurality of patients. The system includes one or more data acquisition devices associated with each of the plurality of patients to obtain monitoring data from each of the plurality of patients. A data acquisition module coupled to the data acquisition devices associated with each of the plurality of patients receives and records the monitoring data. A data analysis module operates to compare the monitored data from each of the plurality of patients to an alert threshold for each type of monitored data for that patient and generates an enhanced threshold alert in the patient window when the monitored data for that patient exceeds the alert threshold for the type of monitored data. The system further includes a detection module that monitors the number, frequency and/or combined duration of the threshold alerts that occur for each patient over an analysis period and generates an indicator in the patient window assigned to the patient when the threshold alerts over the analysis period exceeds an enhanced alert threshold.

Various other features, objects and advantages of the invention will be made apparent from the following description taken together with the drawings.

BRIEF DESCRIPTION OF THE DRAWINGS

The drawings illustrate the best mode presently contemplated of carrying out the disclosure. In the drawings.

Figure 1:
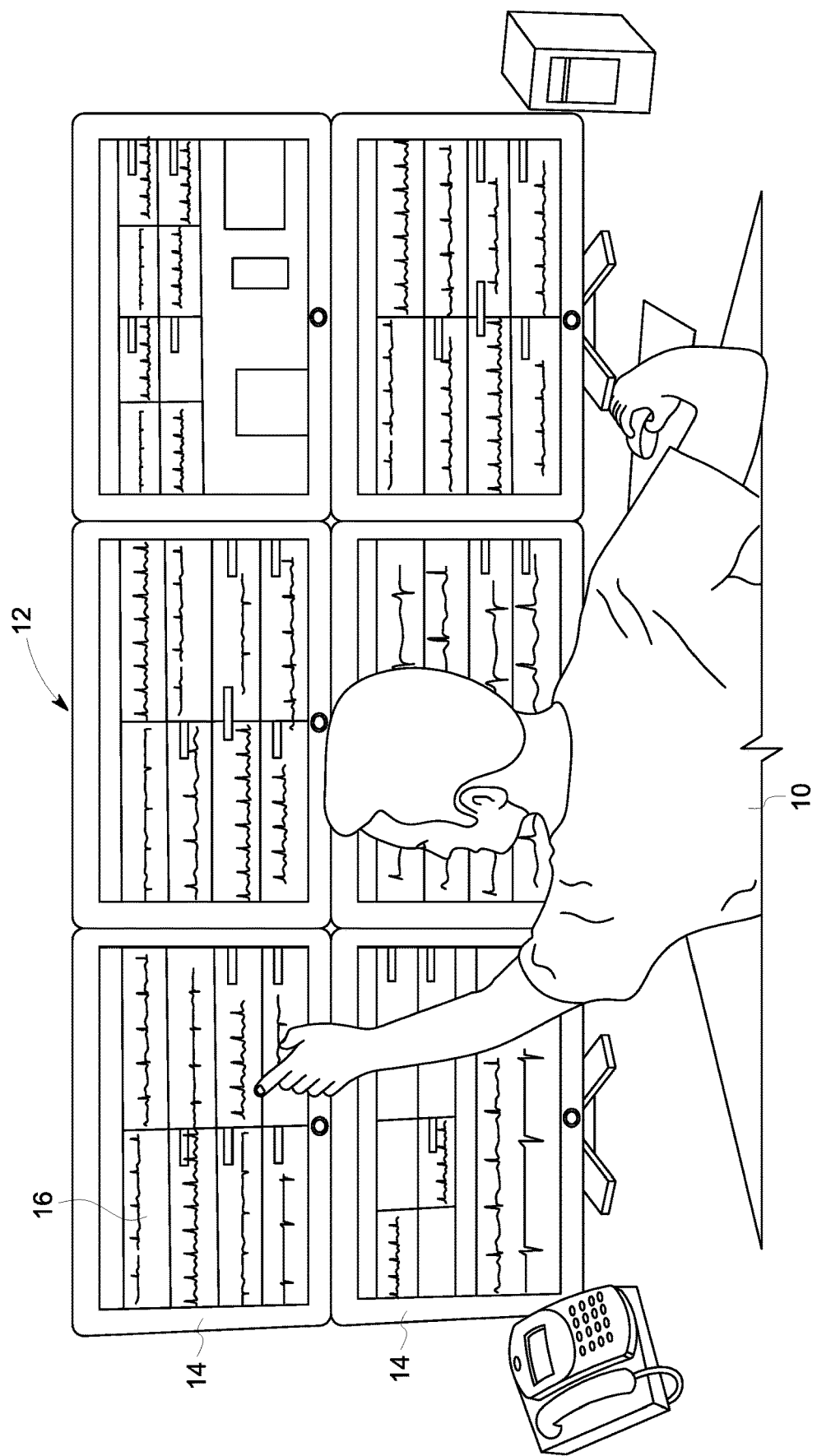
FIG. 1 is an illustration of a monitoring technician monitoring a plurality of patients from a central monitoring station including a multi-patient monitoring display.

The drawings illustrate specific aspects of the described components, systems, and methods for monitoring a plurality of patients. Together with the following description, the drawings demonstrate and explain the principles of the structures, methods, and principles described herein. In the drawings, the size of components may be exaggerated or otherwise modified for clarity. Well-known structures, materials, or operations are not shown or described in detail to avoid obscuring aspects of the described components, systems, and methods.

DETAILED DESCRIPTION

One or more exemplary embodiments of the present disclosure are described below in order to provide a thorough understanding. The described embodiments are only examples of the systems and methods for monitoring either a plurality of patients at a single location or monitoring a single patient at a single location. The skilled artisan will understand that specific details described in the embodiments can be modified when being placed into practice without deviating from the spirit of the present disclosure.

When introducing elements of various embodiments of the present disclosure, the articles "a," "an," and "the" are intended to mean that there are one or more of the elements. The terms "first," "second," and the like, do not denote any order, quantity, or importance, but rather are used to distinguish one element from another. The terms "comprising," "including," and "having" are intended to be inclusive and mean that there may be additional elements other than the listed elements. As the terms "connected to," "coupled to," etc. are used herein, one object (e.g., a material, element, structure, member, etc.) can be connected to or coupled to another object regardless of whether the one object is directly connected or coupled to the other object or whether there are one or more intervening objects between the one object and the other object. In addition, it should be understood that references to "one embodiment" or "an embodiment" of the present disclosure are not intended to be interpreted as excluding the existence of additional embodiments that also incorporate the recited features.

FIG. 1 illustrates a monitoring technician 10 in a working environment in which the monitoring technician 10 is tasked with monitoring the current condition of a plurality of patients located in a hospital environment. In the embodiment shown in FIG. 1, the monitoring technician 10 is shown seated in front of a multi-patient monitoring display 12 that allows the monitoring technician 10 to monitor information about each of the plurality of patients that are located within multiple rooms within a hospital. The multi-patient monitoring display 12 shown in FIG. 1 is comprised of a series of individual monitors 14 that are positioned in a viewing array. Each of the individual monitors includes multiple patient windows 16 that each present monitored data from an individual patient within the hospital environment. Throughout the present disclosure, monitored data will be referred to as physiological, technical, and status-related data obtained when monitoring a patient. The examples used in the present disclosure focus on ECG aspects of the acquired patient monitor date which can include the ECG signal(s), artifact determination, lead connection status, events and alerts (e.g., dysrhythmias, alarm limits, system, technical, etc.). However, it should be understood that the monitored data could be include many other types of patient data obtained by various sensors positioned on the patient and operable to obtain physiological parameters, such as SpO2, CO2, respiration rate, heart rate, invasive blood pressures and the like, from the patient.

As can be understood in FIG. 1, the monitoring technician 10 is in charge of monitoring a large number of patients. Although each of the patient windows 16 will include an alarm or alert that is displayed when the monitored data falls outside of alert threshold values, if the alarm or alert is generated for only a brief period of time before the situation has been corrected, it is difficult, if not impossible, for the monitoring technician 10, who is responsible for many patients, to identify intermittent and continuous alarm conditions that may be temporary in nature but occur a significant number of times over an analysis period. The analysis period can vary depending on the patient and the monitored data, but it is contemplated that the analysis period could be multiple days. In addition, since the monitoring technician 10 works only a specified number of hours during a shift, changes in monitoring technicians 10 throughout a day and during the multi-day analysis period can further exasperate the issue; namely that the monitoring technician is not able to identify trends that occur in the generation of alarms or notifications over a period of time. Shift changes only exacerbate the issue as the new monitoring technician assumes oversight responsibilities for a new set of patients and has limited history of the patient's ongoing monitoring session. The inability to recognize the longitudinal nature of alarm or notification history is an identified problem solved by the inventor of the present disclosure.

Figure 2:
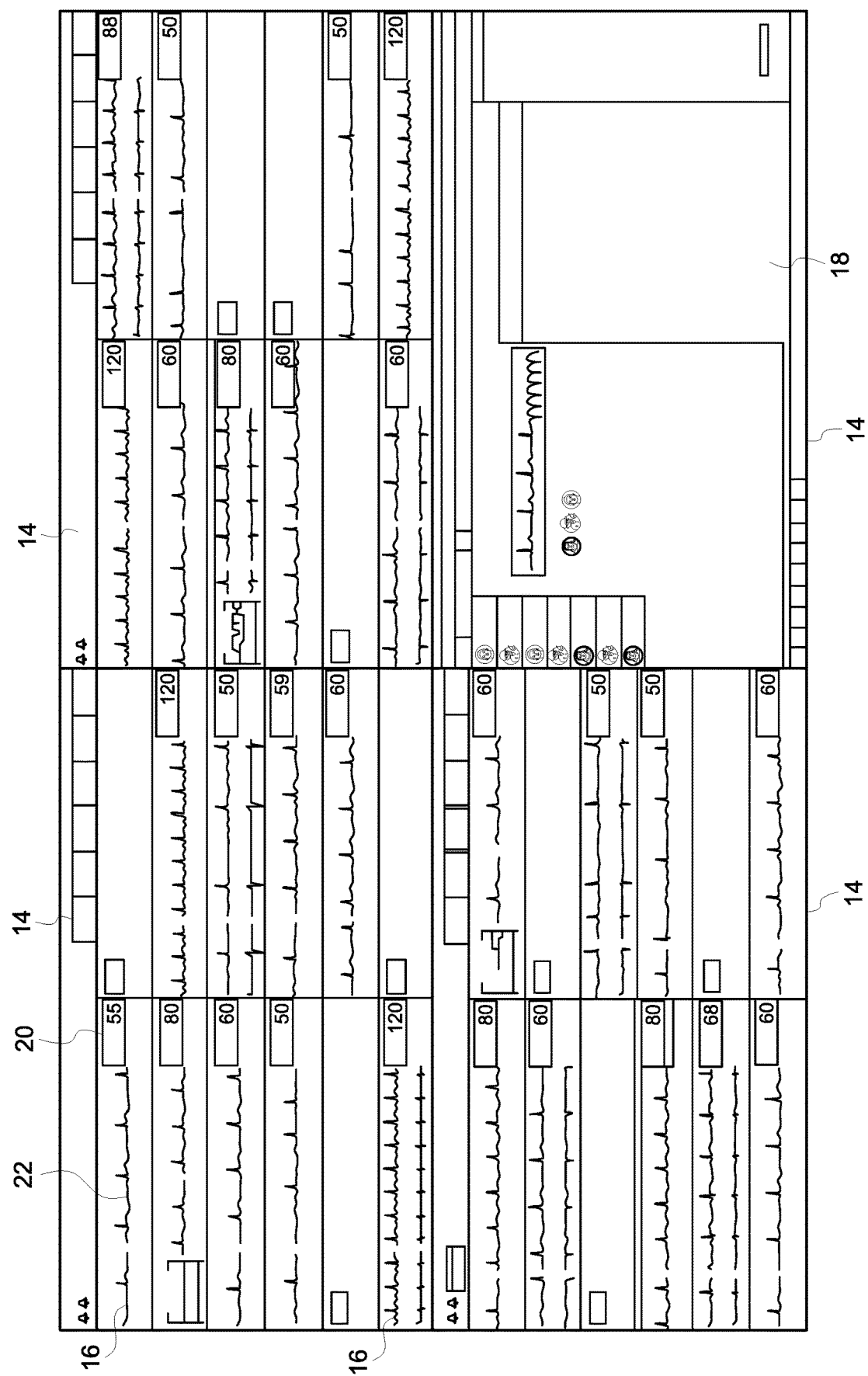
FIG. 2 is a magnified view of four monitoring screens, each including up to twelve patients being monitored by the monitoring technician.

FIG. 2 is a magnified view of four monitors 14 that each include twelve patient windows 16, where each patient window 16 presents monitored data for review by the monitoring technician. The lower monitor 14 shown in FIG. 2 illustrates the ability of the monitoring technician to recall, access, and interpret in a longitudinal context additional information about any one of the patients being monitored and take additional actions utilizing a secondary screen 18 that is available to the monitoring technician. The secondary screen 18 shown in FIG. 2 allows the monitoring technician to send notifications or messages to selected healthcare providers utilizing multiple different types of communication systems. In addition to the secondary screen 18 shown in FIG. 2, the monitoring technician can pull up specific data recorded for each of the individual patients for further analysis and review when desired.

In each of the exemplary patient windows 16 shown in FIG. 2, the monitoring technician can view the heart rate 20 and ECG trace 22 in real time for each of the individual patients being monitored. Additional information can be presented to the monitoring technician in any one of the patient windows 16 depending upon the type of physiological parameters being monitored from the individual patient. Each of the patient windows 16 can show monitored data that is acquired from a separate telemetry device that obtains one or more physiological parameters or could be from a bedside monitor that obtains one or more parameters from the patient.

Figure 4:
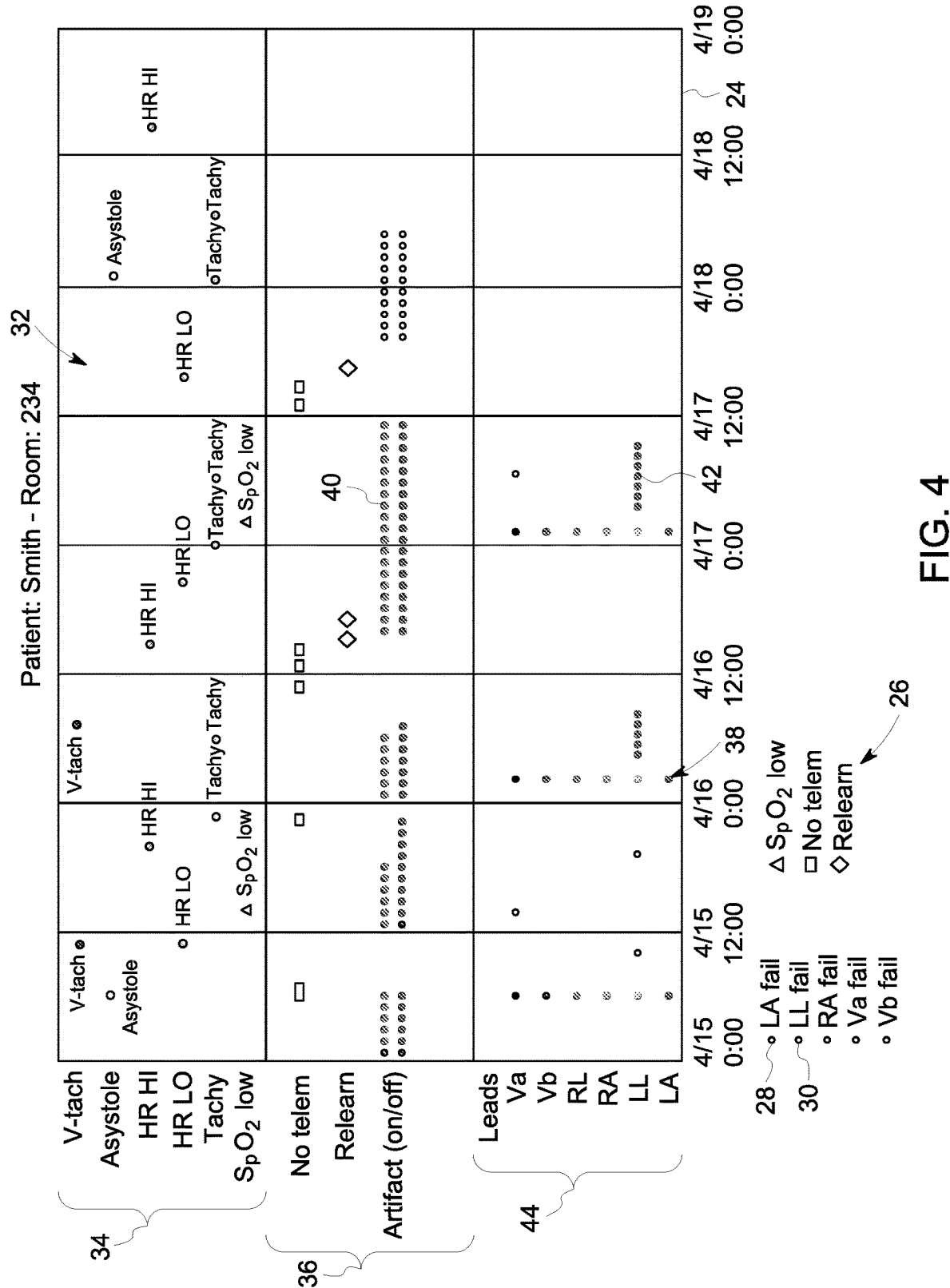
FIG. 4 is a visual display showing the occurrence of various threshold alerts that occur over an analysis period of four days of patient monitoring.

FIG. 4 is a representative image showing the monitored data obtained from a patient over a multi-day monitoring and analysis period. In the embodiment of FIG. 4, the monitored data from the patient is shown for the time period indicated on the horizontal axis 24, which is a period of four days. The image of FIG. 4 illustrates the number of alarms/alerts that are generated for a single patient for a non-limiting number of different types of monitored data over the analysis period. Although representative alarms/alerts are shown for simplicity, there could be many more alarms/alerts shown and monitored on the display of FIG. 4. The alerts can be of varying frequency and duration and can occur as a single event/alert or can occur simultaneously with other alerts. The patient monitored data shown in FIG. 4 is for the patient while the patient's ECG is being monitored in the hospital environment. The image shown in FIG. 4 includes an exemplary, simplified index 26 listing examples of different types of alarms/alerts that are being generated during the monitoring of the patient along with a visual indicator for that type of alarm/alert.

The alert display screen 32 is broken down into multiple sections where the alerts/alarms that are generated during the four-day monitoring and analysis period are grouped together. The upper portion 34 of the alert display 32 includes physiological alerts that are related to the monitored physiological data from the patient. This portion of the display screen 32 includes physiological related alerts and parameter limit violations, such as tachycardia, ventricular tachycardia, premature ventricular contractions, asystole, pauses, SpO2 high/low and heart rate high/low. As can be seen in this portion of the alert display, some alerts take place a significant number of times over the four-day monitoring and analysis period. Each of these individual alerts would be presented in the patient window 16 for varying lengths of time but may be present for only a brief period of time. Since these alerts/alarms are often short in duration and may be less significant for a single occurrence, the monitoring technician may not need to immediately respond to the alarm/alert when the alert happens. Since many of these alarms/alerts occur intermittently and for short periods of time, it is difficult for the monitoring technician to recognize and contextualize trends or repeated alerts as they occur over the four-day analysis period shown.

The middle section 36 of the display 32 includes technical alerts that are related to the operation of the system, such as no telemetry, artifact presence, and the need to enter into the relearn mode. Other types of alerts could also be included in this section of the display 32.

The status of each of the leads used to obtain the ECG monitored data is displayed in the lead status section 44 of the alert display screen 32. As can be seen in the lead status section 44, there are times, such as shown by reference numeral 38, when all of the leads are intentionally or inadvertently removed from the patient such as during movement of the patient, testing, bathing, changing electrodes or for other reasons. In addition, there are times when there is significant movement, poor electrode contact or adherence, etc. and the ECG leads are attached to the patient, which may result in a series of varying length or continuous artifact alerts, such as shown by reference numeral 40. At other times, such as shown by reference numeral 42, a large number of alerts are generated for a lead failure. For example, if a lead is attached to the patient and has poor contact with the patient, the lead falls off, or becomes disconnected, the lead failure alert will be created by the monitoring system, alerting the monitoring technician. Changing electrode-skin contact, reconnecting the leads, etc. may cause the alert to stop but will be reasserted if the condition changes again. This intermittent generation of alerts/alarms makes it difficult if not impossible to grasp the frequency or duration over a period of time and thus is very difficult to detect by the monitoring technician since each alert may occur for a brief period of time and may be self-corrected based upon movement of the patient. The lead status section 44 shows alerts generated when there are various different lead status problems, such as a lead failure, a bad wire, removal of a lead, no telemetry alerts (e.g., out of range), older electrodes, and poor skin preparation which will cause bad contact between the electrode and the patient.

The longitudinal alert display 32 shown in FIG. 4 is an illustration of the various different non-limiting types of alerts and alarms that are generated utilizing currently available patient monitoring systems, such as shown in FIGS. 1 and 2. The alert display 32 shown in FIG. 4 illustrates a large number of alerts/alarms that can be generated for a single individual patient over an example four-day monitoring and analysis period. The alert display 32 shown in FIG. 4 is available for each patient and further emphasizes the number of alerts/alarms that can be generated by the multiple patients being monitored by the monitoring technicians over the monitoring and analysis period. As an illustrative example, reference numeral 42 refers to the LA lead being frequently disconnected/not making proper contact. Other leads could also be off at the same time, such as the Va or Vb leads as an example. When analyzing the alerts shown in FIG. 4, the longitudinal importance of the alerts can depend upon either the frequency of the alerts and/or the frequency of the alerts and the overall duration of the alerts. Different types of trend and smoothing techniques can be used to analyze the alerts taking into account both the frequency of the alerts and the duration of the alerts.

Figure 5:
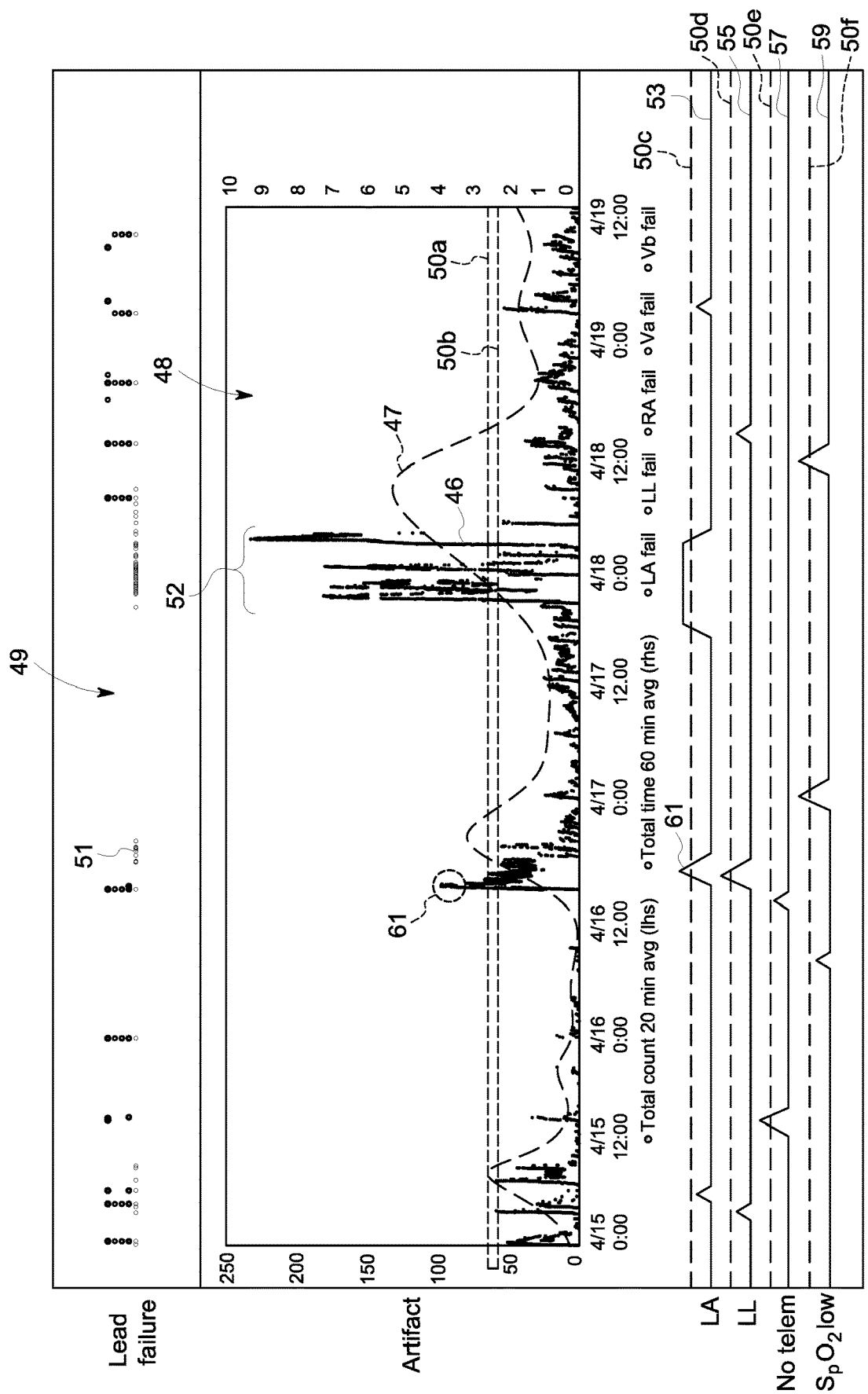
FIG. 5 is a display showing the exemplary occurrence of artifact alerts that occur over the analysis period of patient monitoring.

FIG. 5 is another representative image showing the monitored data obtained from a patient over the same four-day monitoring and analysis period. The trace 46, which is an ECG artifact-based example, represents an exemplary time series smoothing approach with a twenty-minute moving average of the total alert frequency/count while trace 47 is a sixty-minute moving average of the total time in alert shown over the four-day monitoring and analysis period. In the monitor alert interpretation display 48 of FIG. 5, a determined artifact-specific enhanced threshold 50a is shown for the twenty-minute moving average, which is set at sixty-five alerts per twenty minute threshold. The enhanced threshold 50b is shown for the sixty-minute moving average of the total time in alert and is set at 2.5 minutes of artifact alert per the sixty minute threshold. In addition to the traces 46 and 47, lead failures 51 are shown in the upper portion 49 of the display. In the time periods shown by reference numeral 52 and reference numeral 61, a significant number of artifacts (i.e., over sixty-five artifact alerts per twenty minutes in the illustrated example) are detected and may be indicated to the monitoring technician each time they occur. The present disclosure addresses this issue by providing a contextual enhanced alert or "meta-alert" and supporting visual aids identifying these sustained alert cases for each parameter or combinations of parameters. In the embodiment shown in FIG. 5, the enhanced threshold 50a is set for the moving average of the number of artifacts that occur over a selected period of time. As an illustrative example, the enhanced threshold 50a could be set at an intensity of sixty-five occurrences over a twenty minute period. It should be understood that the enhanced threshold 50a is set separately for each type of alert being monitored and that the intensity could be changed/modified by each facility. When the tracked moving average exceeds the enhanced threshold 50a, an enhanced alert is generated. Such enhanced alert will allow the monitoring technician who is managing multiple patients to recognize the repeated generation of individual artifact alerts, understand the longitudinal context of the frequency of the alerts, individual alert duration, the accumulated duration of the alerts, and the potential repeated and sustained nature of the alerts. Without such an enhanced alert, it is very difficult for the monitoring technician to grasp the frequency and duration of the artifact alerts.

As can be understood by the review of FIGS. 4 and 5, the monitored data for each individual patient can be recorded and stored for a monitoring and analysis period, such as the four-day monitoring period shown in FIGS. 4 and 5. Although a monitoring technician may be able to appreciate problems that occur repeatedly over the four-day monitoring period when presented with separate images of FIG. 4 for many patients that need to be reviewed throughout the day, such as shown in on the multi-patient display 12 in FIG. 1, the monitoring technician is not able to recognize trends or higher frequency alerts that may be occurring over a period of time.

The image of FIG. 5 can also include additional traces and enhanced alert thresholds for other monitoring parameters or factors applying similar exemplary trend and smoothing techniques. As illustrative enhanced alerts examples, a lower trace 53 shows a frequency or time in alert moving average and an enhanced threshold of 50c set for when the LA lead is off, trace 55 that shows an enhanced threshold of 50d for when the LL lead is off, trace 57 shows an enhanced threshold of 50e for NO TELEM over the analysis period and trace 59 shows an enhanced threshold of 50f for SpO2 below a lower limit. In each of the lower traces, the portion of the trace identified by reference number 61 is an indication that the tracked moving average of the number, frequency or combined duration of the alerts exceeds the enhanced threshold for the example monitored parameter. The peak 61 is also shown for the trace 46 which is a time when the artifact alerts exceed the enhanced threshold 50a in the upper portion of the display 48.

Figure 3:
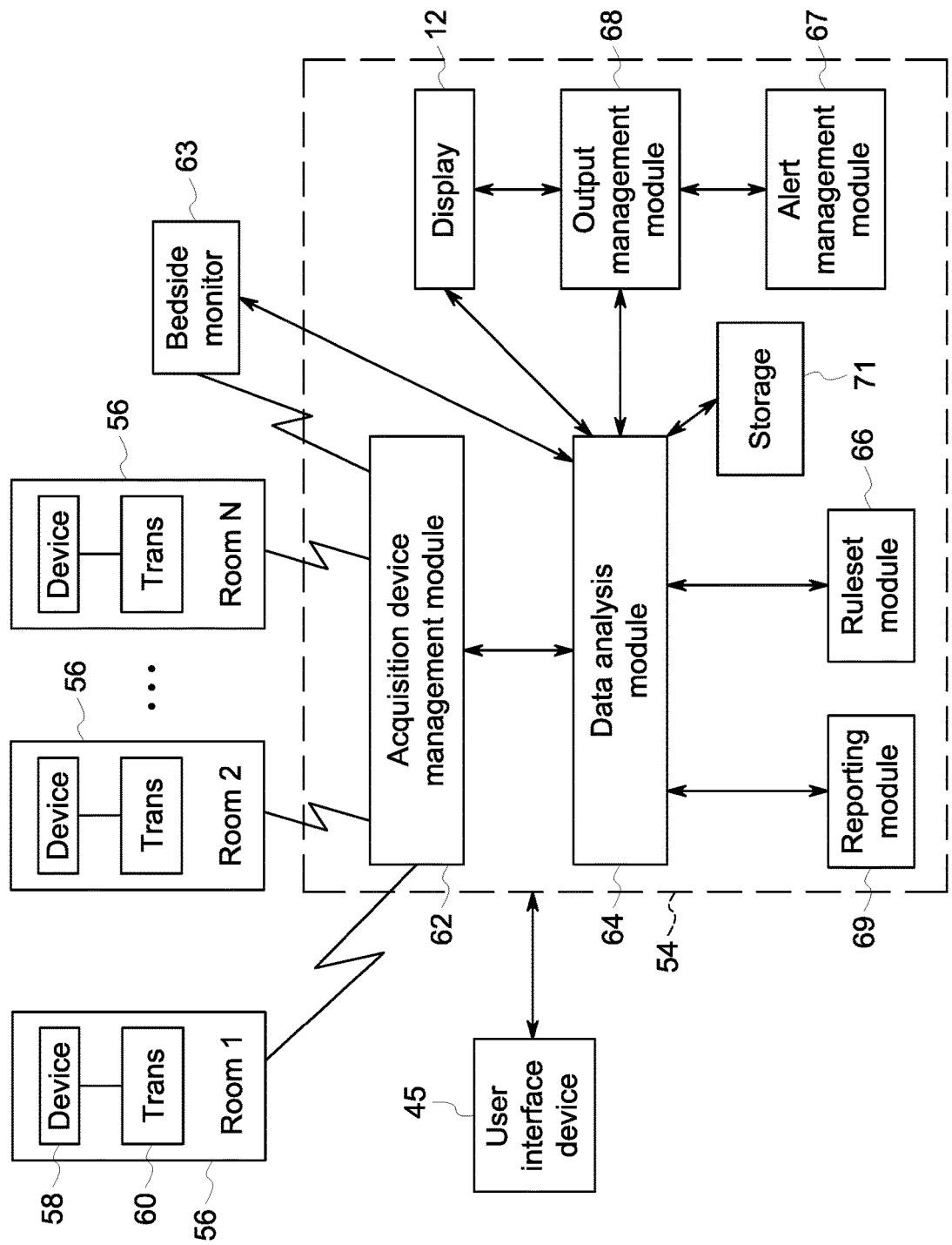
FIG. 3 is a block diagram of the system for monitoring a plurality of patients.

Referring now to FIG. 3, there shown is a patient monitoring system 54 that operates in accordance with an exemplary embodiment of the present disclosure. Many of the components of the patient monitoring system 54 are currently known and being used in the wireless monitoring of patients located throughout a hospital environment. The patient monitoring system 54 includes some type of user interface device 45 having a user interface that allows a user to interact with the patient monitoring system 54 for controlling and modifying various administrative tasks, updating or changing rulesets, setting up reports, etc. The user interface device 45 could be many types of devices, such as a touch screen, keyboard, touch pad or any other similar device.

In the example patient monitoring system 54, the system monitors individual patients that are located in alone or with another patient or patients in a room 56. Each room includes at least one acquisition device 58 that is able to obtain monitored data from the patient. In some cases, multiple acquisition devices 58 could be located in the room to acquire different physiological parameters from the patient. The acquisition device/devices may include ECG leads, a pulse oximeter, blood pressure monitor, or any other type of acquisition device that is able to obtain monitored data from a patient located within the room 56. Although the embodiment of FIG. 3 contemplates a single patient located in each of the rooms 56, multiple patients could be located in each of the rooms where each patient is monitored by one or more separate acquisition device or devices 58.

The acquisition device 58 is connected to a transceiver 60 that is operable to wirelessly transmit the monitored data from the room 56 and the patient. The transceiver 60 is able to communicate information utilizing one of a wide variety of wireless communication techniques, including but not limited to Wi-Fi. Although only a single acquisition device 58 is associated with each room 56 in the embodiment shown in FIG. 3, it should be understood that more than one acquisition devices 58 could be utilized with each patient such that multiple different types of monitored data can be collected from the devices and transmitted, communicated, or delivered to the acquisition device management module 62 wirelessly or via a hardwired connection depending upon the device. In addition to separate acquisition devices 58, a bedside patient monitor 63 could also be used to obtain monitored data from the patient and communicate the monitored data to the acquisition device management module 62 wirelessly or via a hardwired connection. The bedside patient monitor 63 would include a display as is conventional. It is also contemplated that the acquisition device 58 could include an integral display or could be connected to a display located within the room 56.

In the embodiment shown in FIG. 3, each of the patients being monitored is associated with one of the wireless transceivers 60 such that the monitored data can be wirelessly transmitted to the patient monitoring system 54 constructed in accordance with the present disclosure. The patient monitoring system 54 can be located anywhere within the hospital environment as long as the patient monitoring system 54 is able to receive the monitored data from each of the data acquisition devices associated with the plurality of patients being monitored. The patient monitoring system 54 could also be located remotely from the hospital environment. In such case, each of the transceivers 60 would communicate to a wide area wireless network and the patient monitoring system 54 would connect through the same wide area network.

In the embodiment shown in FIG. 3, the patient monitoring system 54 includes an acquisition device management module 62 that is operable to oversee the recording of the operational status of each of the acquisition devices 58. The acquisition device management module 62 is operable to receive and record information related to each of the acquisition devices 58, which data may include information related to the device hookup and removal times. In addition, the acquisition device management module 62 is able to capture information that can include the conditional states of the individual ECG leads attached to the patient, failure in the telemetry that allows the wireless communication of monitored data, the entry of the acquisition device 58 into a relearn condition. In addition to capturing information as to the status of the acquisition device 58, the acquisition device management module 62 is also able to capture the monitored data received from each of the acquisition devices 58, which can include ECG output data, heart rate, respiration measurements, SPO2 values, and parameter or system status information. The acquisition device management module 62 can be part of a computer system located within the hospital environment that is able to receive the monitored data received from each of the wireless transmitters or could be a remote data center.

Although the acquisition device management module 62 is shown in direct communication with the devices 58 and beside monitor 63, it is contemplated that in some implementations, a data aggregator and storage components could be positioned between the devices 58 and the module 62. In each case, monitored data from the patient is received at the acquisition device management module 62 for further processing.

The acquisition device management module 62 is in communication with a data analysis module 64, which also forms part of the patient monitoring system 54. The data analysis module 64 is operable to apply algorithmic/machine learning methods to the captured data received by the acquisition device management module 62. The data analysis module 64 includes internal software and operating programs that allow the data analysis module 64 to perform multiple different functions and analysis on the information acquired from each of the individual patients. As an illustrative example, the data analysis module 64 is able to calculate trends and trend deviations in the monitored data. The data analysis module 64 is able to apply data smoothing methods such as averaging, weighted and exponential smoothing methods to identify trend exceptions in the monitored data obtained from each of the individual patients. In addition, it is contemplated that advanced machine learning could be used as part of the data analysis module 64 to identify trend exceptions in the monitored data and set enhanced alert threshold levels for a given parameter or combination thereof. The operating programs and systems on the data analysis module 64 are able to monitor and analyze conditional states, such as but not limited to lead failure by each individual lead, situations when no telemetry is available, when the system is in a relearn mode, conditions when arrhythmia analysis is suspended.

Although examples of the different types of data analyses that can be carried out by the data analysis module 64 are described, it should be understood that a wide number and variety of different types of data analysis techniques, including algorithmic/machine learning methods could be utilized to monitor and analyze the monitored data available from each of the plurality of patients. The data analysis module 64 is able to compare not only the current information received from each of the patients, but also to analyze the monitored data from each of the patients over a longitudinal period of time, which will be referred to as an analysis period. The analysis period can be hours, days or even weeks depending upon the amount of time the patient is being monitored. As indicated above, many trends in artifacts or lead failures may not be identifiable on a real time basis and the use of the data analysis module 64 will allow the patient monitoring system 54 to identify and contextualize these trends over the analysis period.

In the embodiment shown in FIG. 3, the data analysis module 64 is in communication with a ruleset module 66. The ruleset module 66 acts as a depository of information that can be utilized by the data analysis module 64 when analyzing the monitored data received from each of the patients. The ruleset module 66 is used to set and record alert thresholds for each of the different types of monitored data such that the data analysis module 64 can compare monitored data from each of the patients to alert thresholds. In addition, the ruleset module 66 can be used to record and store enhanced alert thresholds, which are used to generate enhanced alerts when a monitored parameter or data from the patient indicates that a trend has been occurring over time that needs to be identified and brought to the attention of the monitoring technician. The parameters in the ruleset module 66 can be user selected or can be pre-stored within the ruleset module. The ruleset module 66 allows the threshold and parameters to be updated and modified based upon hospital settings or based upon each individual patient's history and condition. Further, the ruleset module 66 allows each parameter's threshold to be optimized with various techniques to determine the ideal sensitivity and specificity of the alert for a patient or a population of patients, as shown in FIG. 5 with the artifact example.

The data analysis module 64 is in communication with the multi-patient monitoring display 12 such that the data analysis module 64 can create an indicator on the monitoring display 12 depending upon the results of the data analysis that occurs within the data analysis module 64. As an example, informational text or visual indicators can be presented in each of the individual patient windows depending upon the longitudinal data analysis carried out by the data analysis module 64. The data analysis module 64 could also be in communication with the bedside monitor 63 to present the informational text and/or visual indicators on the display of the bedside monitor 63. In embodiments in which the data acquisition devices 58 include a display or are connected to a display, the data analysis module 64 would communicate to the acquisition device 58 to present the informational text and/or visual indicators. Further information about the different types of indicators that can be presented to the monitoring technician within any one of the individual patient windows on the multi-patient monitoring display 12 will be discussed in greater detail below. However, it should be understood that the indicator is used to indicate and contextualize a longitudinal trend that has occurred over time in one of the monitored data parameters from the patient, where such indicator was not previously available in monitoring systems that monitor the current data obtained from the patient without utilizing historic information relating to trends and alerts generated based upon the monitored data from the patient.

The patient monitoring system 54 further includes an output management module 68 that receives information from the data analysis module 64 and operates to provide a summary of contextual information for reporting, rules-based engine flagging or care team/clinician review. As an illustrative example, the output management module 68 can generate reports to a patient care technician at a shift change utilizing either electronic or paper reporting through a connection to a display or some type of printing device. The output management module 68 can further send alerts to the patient care technician utilizing various different types of alert notification systems. The alerts are illustrated by reference numeral 67 and can be generated utilizing various different types of alert techniques, such as paging, texting or any other type of notification system that may be available in the hospital environment.

In the embodiment illustrated, the data analysis module 64 could also be in communication with the reporting module 69 and a data storage element 71. The reporting module 69 can be used to control various different reporting methods for the patient monitory system 54 while the storage element 71 would allow for data storage and later processing.

Figure 6:
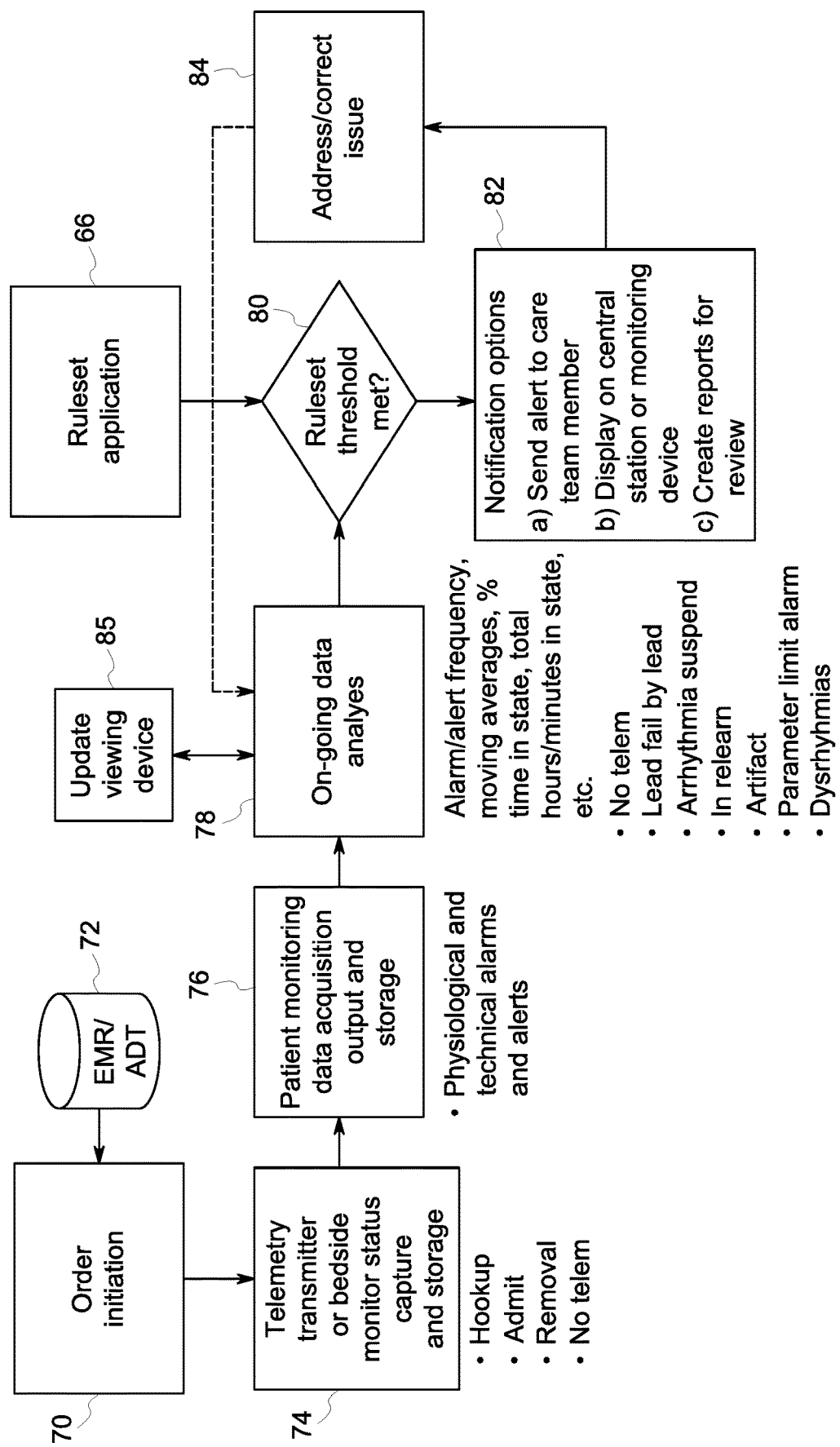
FIG. 6 is a flow chart illustrating the sequence of operation for the patient monitoring method.

FIG. 6 illustrates a flow chart of the operation of the patient monitoring system 54 configured and constructed in accordance with the present disclosure. The flow chart of FIG. 6 will be described with reference to the system diagram previously described in FIG. 3. Initially, in step 70, an order is given to monitor a patient utilizing a wireless monitoring device or bedside monitor. The wireless monitoring device or bedside monitor can retrieve information about the patient from an electronic medical record obtained from database 72.

In step 74, the transmitter used to relay information from the acquisition device associated with the patient provides monitoring status information, which can include the time of connection, the removal completion time and other information related to the communication needed to relay monitored data from the patient to the patient monitoring system of the present disclosure. In step 76, the transceiver associated with the patient transmits information to the acquisition device management module of the patient monitoring system. This information includes alarms and alerts, the actual monitored data from the patient, along with any other information that is typically transmitted from an acquisition device for monitoring and analysis by the patient monitoring system.

In step 78, the data analysis module 64 performs ongoing data analysis on the monitored data obtained from each of the individual patients. As described previously, the data analysis module 64 is able to carry out a wide variety of analysis on the monitored data, which can include alarm/alert frequency obtained from the patient. In an exemplary case, the data analysis module can determine in step 78 periods of no telemetry, when individual leads have failed, when arrhythmia detection has been suspended, when the system is the relearning process and periods when relatively significant artifacts are present. Based upon the analysis of the data in step 78, the method moves to step 80 in which the data analysis module compares the information to rulesets obtained from the ruleset module 66. As indicated previously, in step 80, the data analysis module 64 compares the number, frequency and/or combined duration of threshold alerts that occur to a series of enhanced alert thresholds that are obtained from the ruleset module 66. An enhanced alert threshold is a threshold that indicates when a parameter's data series is analyzed for frequency, time/duration, etc. in alert via a smoothing algorithm or machine learning and exceeds a determined value over time. Alternatively, the aggregated amount of time that an alert is being generated over the total number of alerts can be monitored to provide another basis for generating an alert to the clinician.

In yet another contemplated embodiment, the enhanced alert can be generated based on a composite of threshold alerts that are generated for similar categories of alerts. For example, if the LA lead is disconnected a number of times for varying durations, the number of alerts based on the LA lead could be combined with the number of alerts generated for the LL lead. In such case, the number and duration of the alerts for the combination of both the LA and LL leads would be aggregated to determine if an enhanced alert should be generated during the analysis period based on the aggregation of the lead failure alerts. Another possible category of alerts could be the combination of alerts related to heart rate and SpO2. Since SpO2 and HR-high and HR-low are related, grouping these alerts for analysis would provide another basis for generating the enhanced or "meta" alert. When this grouping of alerts becomes frequent and sustained, the system would create an enhanced alert. The creation of grouping of related alerts is another way to alert a monitoring technician of frequent and sustained alerts that may otherwise go unrecognized or need to be addressed clinically such as changing the alarm limit settings of the monitor to lessen alarm fatigue. The enhanced alert threshold can be set for each of the numerous types of monitored data from the patient and/or for the groupings of alerts. The enhanced alert thresholds can also be different for different analysis periods for the different types of monitored data.

As an illustrative example, if the left lead (LA) has failed more than twenty times over an analysis period, which may be over a few or several hours, the data analysis module 64 determines that an enhanced indicator should be presented to the monitoring technician indicating and alerting the number of alerts/alarms over an analysis period and that corrective action should take place. The enhanced alert threshold is thus violated and enhanced indicator should be generated. The enhanced alert threshold may be a small number of threshold alerts for a shorter period of time or could be the cumulative duration of threshold alerts generated over the analysis period.

In step 82, the data analysis module determines that an enhanced notification must be generated, such as sending a direct alert to a care team member, providing an indicator on the multi-patient monitoring display, adding an alert/graph or gauge to a single patient monitor display or creating a physical report. The various different types of indicators that can be presented on the multi-patient monitoring display will be described in detail below.

In step 80 described above, the data analysis module 64 can compare the number of alerts that have been generated for a specific reason, such as artifact levels exceeding an alert thresholds, lead failure alerts, no telemetry or other alerts that have been generated for an individual patient over an analysis period. The analysis period can vary depending upon the type of enhanced alert that will be generated. In addition, alert thresholds can be different for different analysis periods. As an example, five lead failure alerts generated over a two hour period may violate an alert threshold or ten lead alerts over a three hour period may also generate a similar alert. The enhanced alert threshold is thus based upon the type of alert being monitored and the duration of time the alerts occur. The enhanced alert thresholds are stored within the ruleset module and can be adjusted and modified as needed. The ruleset module 66 is in communication with the data analysis module such that the data analysis module can retrieve stored information as desired.

Referring back to FIG. 6, once the notification has been generated, the system can monitor in step 84 whether the issue has been addressed and modified and return back to the data analysis step 78. In this manner, the patient monitoring system 54 is able to provide a level of longitudinal analysis and contextualizing of alerts and alarms that was not previously available in patient monitoring systems.

As previously described, the data analysis module 64 operates to create a longitudinal analytic based system that generates an indicator when the number of threshold alerts for any one of a variety of monitored parameters exceeds an enhanced alert threshold. The enhanced alert threshold monitors not only the number of alerts/alarms that occur but compares the number to an enhanced alert threshold over an analysis period. If the data analysis module determines that an enhanced indicator should be generated and available to the monitoring technician, the data analysis module creates such an indicator that is shown in the patient window on the multi-patient monitoring display or on the display of a single patient bedside monitor. As shown in FIG. 6, the viewing devices, which can be the multi-patient monitor, a bedside monitor or any other viewing device, is updated in step 85 with the results of the data analysis and the indicator generation. It is envisioned that the user could also accept or acknowledge the enhanced or "meta" alert on the device 56, the bedside monitor 63 or display 12 via an alarm receipt button and report this state back to the longitudinal alert management and interpretation system.

Figure 7:
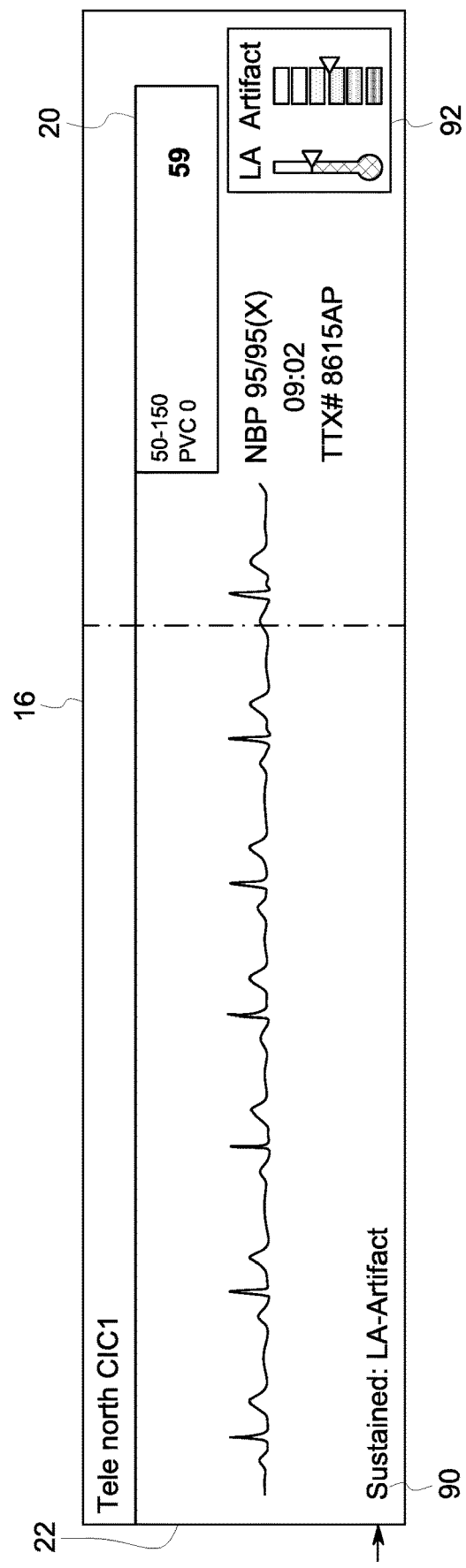
FIG. 7 is a magnified screenshot of a patient window showing the indicator for a sustained artifact in accordance with an exemplary embodiment.
Figure 9:
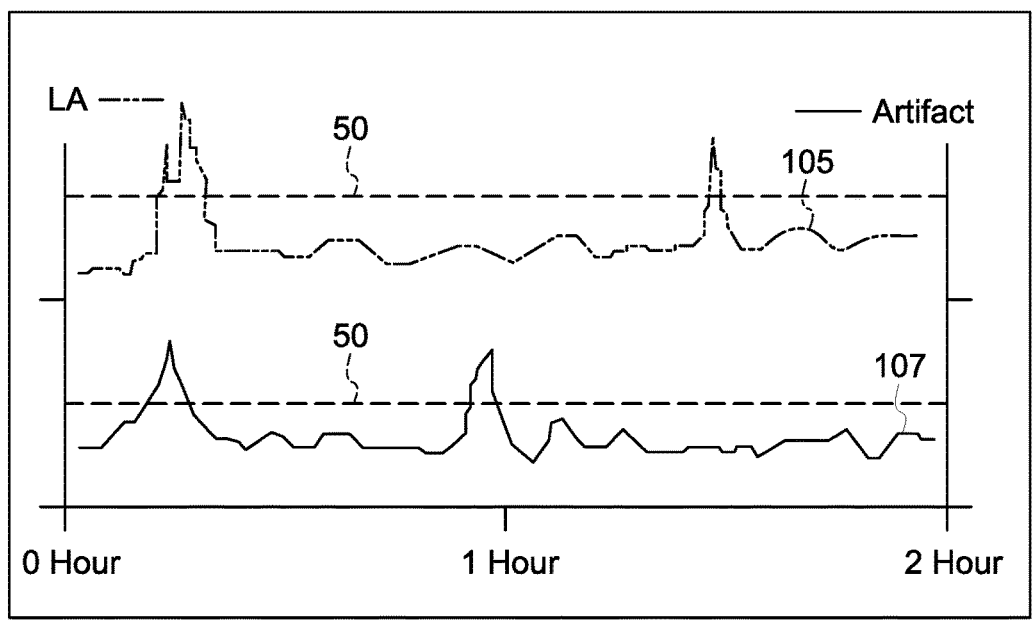
FIG. 9 is a timeline view of two examples of acquired monitoring parameters and their respective moving averages over time and enhanced or meta alert threshold levels.

FIG. 7 illustrates one of the patient windows 16. As previously described, the patient window 16 includes current monitored data obtained from the patient, such as the heart rate and the ECG trace 22. However, when the data analysis module determines that an enhanced indicator should be generated, the data analysis module generates an indicator within the patient window 16. In the embodiment shown in FIG. 7, two separate indicators are shown. The first indicator 90 is a text-based indicator indicating that sustained LA lead failure(s) have been detected. During real time monitoring, if an LA lead failure is detected, the LA lead failure alert text flashes on the screen as long as the lead failure is present. Since the LA lead failure may be present for only brief periods of time, it is difficult for the monitoring technician to keep track of the number of times the LA lead failure text has flashed on each of the individual patient windows. The enhanced indicator 90 remains on the patient window and indicates that a sustained number of LA lead failures have been detected utilizing the method and system of the present disclosure. The text-based indicator 90 can be presented in a bright color, can flash or a combination of both. The indicator 90 is thus based upon a longitudinal analysis of the LA lead failures and is generated only when the number of LA lead failure alerts/alarms exceeds an enhanced alert threshold over an analysis period. The gauges/indicators FIG. 9 is a visual representation of the longitudinal measurement of two measured thresholds, which include system artifact alerts 105 over the analysis period and the LA lead failure alerts 107 over the same analysis period. The analysis period can vary and in the embodiment show, the analysis period is 120 minutes. In FIG. 9, the enhanced alert threshold 50 is shown for each of the measurements. When either of the monitored parameters exceed the enhanced alert threshold 50, an enhanced alert would be generated.

Figure 8:
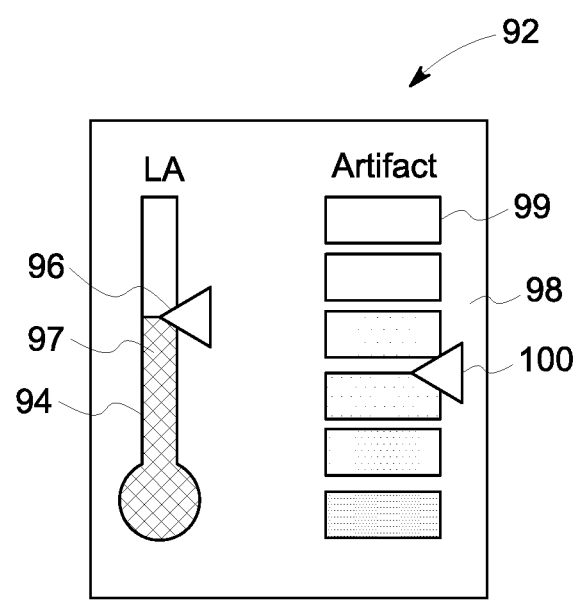
FIG. 8 is a magnified view illustrating one of the possible visual representations.

In addition to or in place of the first indicator 90, a second indicator window 92 can be displayed in the patient window 16, as illustrated in FIG. 7. FIG. 8 provides a magnified view of the indicator window 92. The indicator window 92 includes two different types of visual displays that can show a range of the number of either LA lead failures or artifacts. The first exemplary visual indicator 94 takes the shape of a thermometer where the number of LA lead failures is shown by pointer 96. The pointer 96 moves upward along the thermometer as the number of LA lead failures increases. In addition, a solid color 97 replicates the level of mercury within the thermometer and provides an easy to understand visual indication of the number of LA lead failures.

The second exemplary visual indicator 98 includes a series of bars 99 that are filled in as the pointer 100 moves up the series of bars. Again, the series of bars 99 are illuminated along with the movement of the pointer 100 to visually indicate the number of artifacts that have been sensed over the analysis period. Although FIG. 8 illustrates two different types of visual indicators, the visual configuration of the indicators could change as long as the indicator includes a representation of the current number of alerts relative to a range of alerts.

Figure 10:
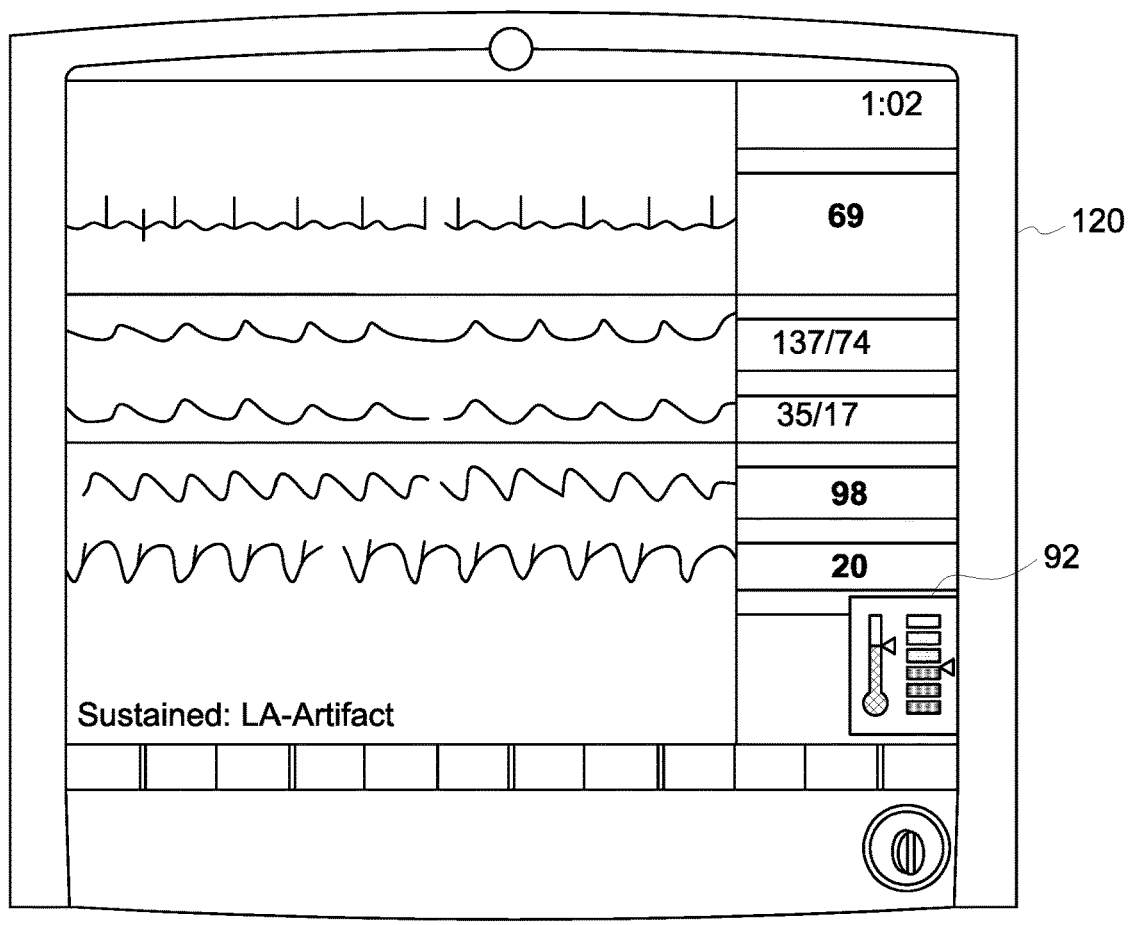
FIG. 10 is a view of a single patient bedside monitor showing the indicator for a sustained artifact in accordance with an exemplary embodiment.

As indicated above, FIG. 7 shows one of the patient windows of a multi-patient monitor. FIG. 10 is a single patient bedside monitor 120 that can include the same second indicator window 92 as described above. In this embodiment, the second indicator window 92 would allow a care team member to be presented with the enhanced alert indicator when the care team member walks into the patient room including the bedside monitor 120.

Figure 11:
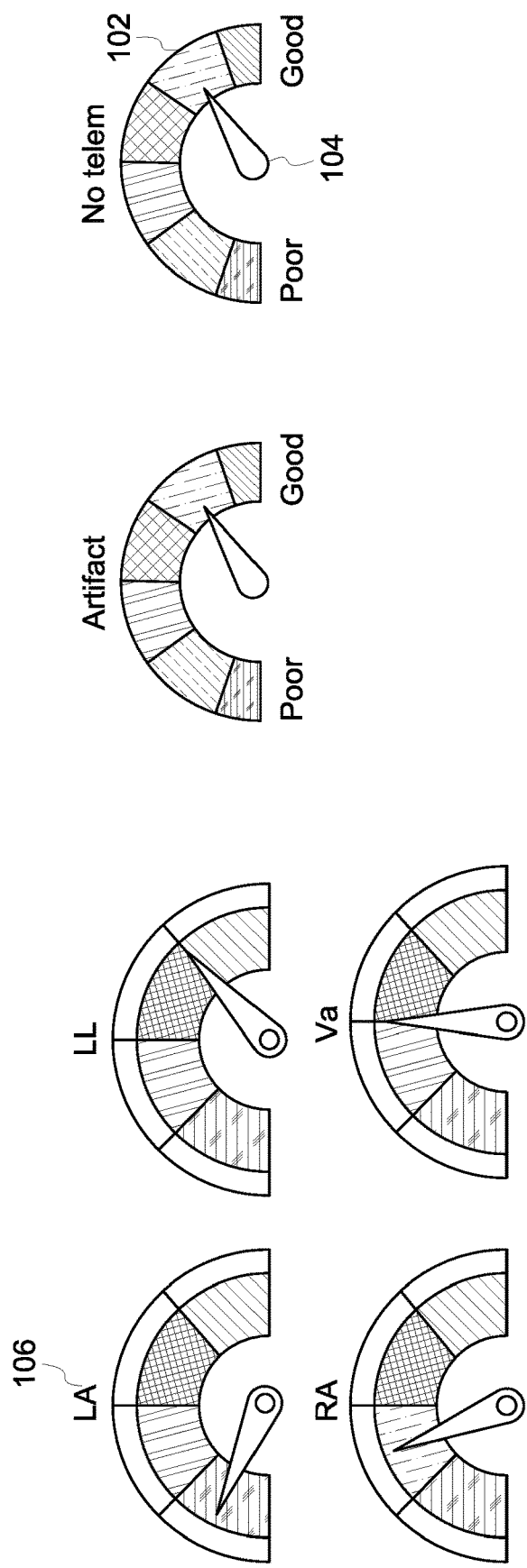
FIG. 11 is a view showing alternate visual representations.

FIG. 11 illustrates yet another type of visual indicator of the threshold alerts that have been generated over an analysis period. In the embodiment of FIG. 11, a series of visual gauges 102 are used along with a movable pointer 104 to indicate the number of alerts generated. In the embodiment shown in FIG. 11, the gauge 102 varies from a "good" to a "poor" value and the position of the pointer 104 along the gauge 102 provides an easy to understand visual indication to the monitoring technician. In the embodiment shown in FIG. 11, the gauge for the LA lead clearly indicates that a significant number of lead failures has occurred and this indicator is presented to the monitoring technician in an easy to understand visual representation. Although various different types of visual indicators are shown and described in FIGS. 7-11, it should be understood that various other types of visual indicators, alarm indicators, and alarm acknowledgement buttons or methods could be utilized while operating within the scope of the present disclosure. In addition, the gauges 102 and indicators 94, 98 do not just show the absolute number of alerts but could be a smoothed or trended parameter in exemplary embodiments. The use of smoothed or trended parameters may be necessary to get the contextual/longitudinal/sustained nature of the frequency or duration.

As can be understood by the above-description, the system and method of the present disclosure allows for the analysis and identification of subpar patient monitoring conditions, such as in an ECG-based patient monitoring system. The subpar monitoring conditions may be due to excessive or continuous alerts, such as lead failures, no telemetry, artifacts, arrhythmia suspend, heart rate, SpO2 or other types of intermittently occurring alerts. The system and method of the present disclosure provides a contextualized, longitudinal-based view of the exemplary ECG acquisition process to improve the identification of alerts that occur over an extended analysis period. The system provides for effective notification and visual display that allows a monitoring technician to view the enhanced notifications from a central station while simultaneously monitoring 36 to 72 or more patients. In addition, the system allows for monitoring the efficiency and effectiveness of monitoring over a floor, unit, or entire hospital.

This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

I claim:
1. A method of monitoring a plurality of patients from a single monitoring location, the method comprising:
receiving monitored data from each of the plurality of patients;
comparing the monitored data from each of the patients to an alert threshold and generating an alert for the patient each time the monitored data violates the alert threshold;
defining a pre-determined analysis period that is a pre-determined amount of time prior to a present time;

monitoring a number, a frequency or a combined duration of a plurality of alerts that occurred for each of the patients over the analysis period;

aggregating the number, frequency, or the combined duration of the plurality of alerts over the analysis period;

comparing the aggregation of the plurality of alerts to an enhanced alert threshold; and generating an enhanced alert indicator for each of the patients on a display in response to the aggregation of the plurality of alerts exceeding the enhanced alert threshold, wherein the enhanced alert indicator triggers the provision of care to the patient by a care giver.

2. The method of claim 1 wherein the plurality of alerts are aggregated using a moving average of the alerts over the analysis period.

3. The method of claim 1 wherein the aggregation step includes determining a total number of alerts over the analysis period.

4. The method of claim 1 wherein a plurality of different types of monitored data are received from the patient, wherein two or more of the plurality of different types of monitored data are grouped together and the enhanced alert threshold is set for the group.

5. The method of claim 1 wherein the display is a multi-patient monitoring display used to simultaneously monitor the monitored data from the plurality of patients, wherein each of the plurality of patients includes a patient window on the multi-patient monitoring display and both the alerts and the enhanced alert indicator are displayed in the patient window for each of the plurality of patients.

6. The method of claim 5 wherein the enhanced alert indicator is generated on the multi-patient monitoring display separately for each of the plurality of patients.

7. The method of claim 1 wherein the enhanced alert indicator on the display includes a visual representation of the number of alerts relative to a range.

8. A method of monitoring a plurality of patients, the method comprising:

providing a multi-patient monitoring display that includes a plurality of patient windows;

receiving a plurality of types of monitored data from each of the plurality of patients;

simultaneously displaying the plurality of types of monitored data from each of the plurality of patients in the patient window assigned to the patient;

comparing the monitored data received from each of the plurality of patients to an alert threshold for each type monitored data and generating an alert in the patient window each time the monitored data exceeds the alert threshold for the type of monitored data;

defining a pre-determined analysis period that is a pre-determined amount of time prior to a present time;

monitoring a number, a frequency or a combined duration of the plurality of alerts that occurred for each patient over an analysis period;

aggregating the number, frequency, or the combined duration of the plurality of alerts over the analysis period;

comparing the aggregation of the alerts to an enhanced alert threshold; and generating an enhanced alert indicator in the patient window assigned to the patient in response to the aggregation of the alerts exceeding the enhanced alert threshold, wherein the enhanced alert indicator for the patient triggers the provision of care to the patient by a care giver.

9. The method of claim 8 wherein the plurality of alerts are aggregated using a moving average of the alerts over the analysis period.

10. The method of claim 8 wherein the aggregation step includes determining a total number of alerts over the analysis period.

11. The method of claim 8 wherein the enhanced alert indicator on the display includes a visual representation of the number of threshold alerts relative to a range.

12. A system for monitoring a plurality of patients comprising:

a multi-patient monitoring display that includes a plurality of patient window each assigned to one of the plurality of patients;

one or more data acquisition devices associated with each of the plurality of patients to obtain monitored data from each of the plurality of patients;

a data acquisition module coupled to the data acquisition devices associate with each of the plurality of patients to receive and record the monitored data;

a data analysis module operable to compare the monitored data from each of the plurality of patients to an alert threshold for each type of monitored data and generate an alert in the patient window each time the monitored data exceeds the alert threshold for the type of monitored data;

a detection module operable to monitor the a number, a frequency or a combined duration of a plurality of alerts that occurred for each patient over a pre-determined analysis period that is a pre-determined amount of time prior to a present time and to generate an enhanced alert indicator in the patient window assigned to the patient when an aggregated number of alerts, frequency of alerts or the combined duration of the plurality of alerts over the analysis period exceeds an enhanced alert threshold, wherein the enhanced alert indicator for the patient triggers the provision of care to the patient by a care giver.

13. The system of claim 12 wherein the enhanced alert indicator on the display includes a visual representation of the number of threshold alerts relative to a range.

14. The system of claim 12 wherein the detection module aggregates alerts using a moving average of the alerts over the analysis period.

15. The system of claim 12 wherein each of the plurality of patients includes a patient window on the multi-patient monitoring display and both the alerts and the enhanced alert indicator are displayed in the patient window for each of the plurality of patients.

* * * * *